United States Patent [19]

Monte et al.

[11] 3,950,133

[45] Apr. 13, 1976

[54] REAGENT FORMULATIONS FOR ASSAYING BIOLOGICAL SPECIMENS AND METHODS OF PREPARING AND USING SAME

[75] Inventors: Alexander A. Monte; Ching Chiang, both of Glendora, Calif.

[73] Assignee: Mallinckrodt, Inc., St. Louis, Mo.

[22] Filed: May 6, 1974

[21] Appl. No.: 467,550

Related U.S. Application Data

[60] Division of Ser. No. 200,552, Nov. 19, 1971, Pat. No. 3,816,262, which is a continuation-in-part of Ser. No. 190,883, Oct. 20, 1971, abandoned.

[52] U.S. Cl. .............................. 23/230 B; 195/63
[51] Int. Cl.² .................................... G01N 33/16
[58] Field of Search ................................ 23/230 B

[56] References Cited
UNITED STATES PATENTS

| | | | |
|---|---|---|---|
| 3,627,688 | 12/1971 | McCarty et al. .................. | 195/63 X |
| 3,663,175 | 5/1972 | Depositar et al. ................. | 23/230 B |

OTHER PUBLICATIONS

Henry, Clinical Chemistry, Principles and Technics, pp. 190–193 (1964) RB40H4 (A.U.171).

*Primary Examiner*—Joseph Scovronek
*Attorney, Agent, or Firm*—Mathew D. Madsen

[57] ABSTRACT

A solid, water-soluble substantially anhydrous, storage-stable reagent formulation for use in conducting a clinical diagnostic test on a biological specimen is provided. The reagent formulation comprises a mixture containing a reagent capable of participating in a test reaction to effect a measurable change in a test system; and a nitrogen bearing polyoxyalkylene nonionic surfactant. The surfactant has a structure corresponding to that obtained when ethylene diamine is reacted sequentially with propylene oxide and ethylene oxide in the presence of a catalyst. The polyoxypropylene chains of said surfactant have an average molecular weight of between about 750 and about 6750. Methods of preparing the reagent formulations and methods of using them to conduct clinical diagnostic tests are also provided.

9 Claims, 1 Drawing Figure

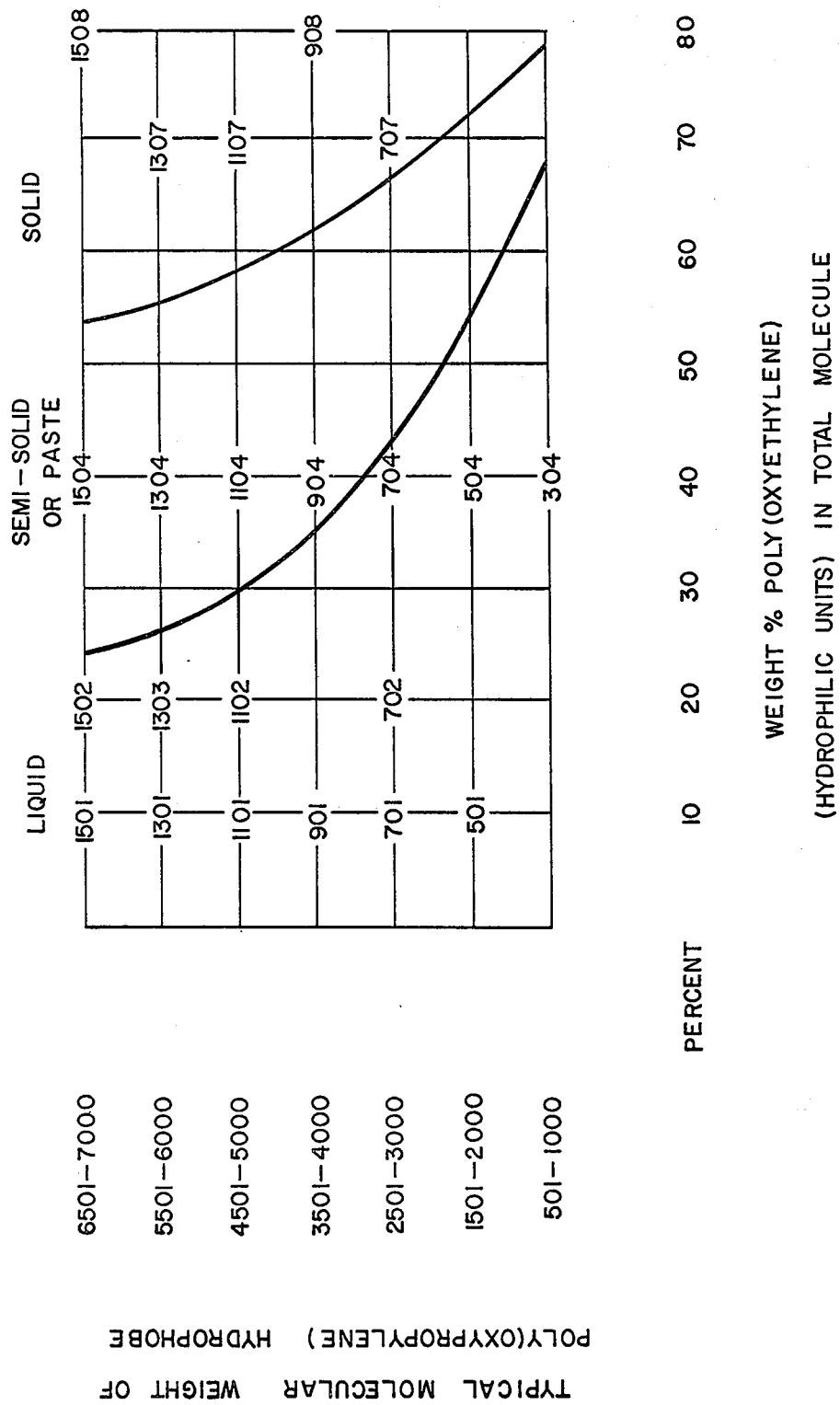

REAGENT FORMULATIONS FOR ASSAYING BIOLOGICAL SPECIMENS AND METHODS OF PREPARING AND USING SAME

CROSS-REFERENCE TO RELATED APPLICATION

This application is a division of our copending, coassigned U.S. Patent Application Ser. No. 200,552, filed Nov. 19, 1971, now U.S. Pat. No. 3,816,262, issued June 11, 1974, which is a continuation-in-part of our U.S. Pat. application Ser. No. 190,883, filed Oct. 20, 1971, now abandoned.

BACKGROUND OF THE INVENTION

This invention relates to the field of clinical diagnostic testing and more particularly to novel reagents and methods for making biological assays on body fluids.

A large variety of test reagents and methods are available for use in determining the character of various body fluids to assist in the diagnosis of certain pathological conditions. Tests for determination of certain types of biological activity or the presence and quantity of certain biologically active components provide information indicating the presence or absence of disease or other physiological disorder. In accordance with such tests, the biological specimen to be analyzed, for example, a sample of a body fluid, is typically mixed with a liquid reagent formulation which contains a reagent capable of effecting a reaction which causes a measurable change in the specimen/reagent system. Very often the reaction which takes place in the test is an enzymatic reaction. Certain tests are designed, in fact, to determine the presence of a particular enzyme and in such cases the reagent formulation may contain a substrate upon which the enzyme to be determined is known to act. In other cases, the determination may be for a material which is known to be a reactive substrate in an enzymatically catalyzed reaction. In either case, the reagent formulation very commonly contains an enzyme, a coenzyme or both. Because the catalytic activity of most enzymes is specific to a particular reaction, test reagents can be formulated which are effective to determine specific biological components or activities even in a complex body fluid containing a large number of other components which might interfere with efforts to obtain a purely chemical analysis. Moreover, many of the components which are to be determined have highly complex chemical structures which would render direct chemical analysis difficult even in the absence of any contaminants.

Unfortunately, enzymes and coenzymes are generally rather delicate materials which may be readily denatured by heating and which also tend to degenerate upon storage. Many of the substrate materials used in biological assay reagent formulations are similarly unstable. Liquid reagents containing such components are therefore not generally susceptible to storage and must be freshly prepared shortly prior to use in clinical diagnostic testing. Because of the relative expense of enzymes and coenzymes and the skill required to prepare a reagent formulation containing these materials which can be utilized to obtain accurate clinical diagnostic test results, the instability of the liquid formulations has motivated a substantial amount of research to develop reagents in a relatively storage-stable form. Much of this effort has been directed to the development of solid, dry, water-soluble formulations which can be dissolved in water at the time of testing to provide a fresh liquid reagent useful in the test. Typical prior art dry reagent formulations are disclosed in Deutsch U.S. Pat. No. 3,413,198 and Stern et al. U.S. Pat. No. 3,546,131.

A dry reagent formulation satisfactory for use in preparing liquid reagents for routine clinical diagnostic tests should satisfy a number of criteria. It must be readily soluble in a solvent compatible with the biological specimen, usually water. It should be capable of solubilizing proteinaceous material in the specimen. Moreover, it should be readily susceptible to packaging in convenient sized packages and be adapted for rapid dissolution in the solvent to provide a liquid reagent of proper strength for a given test or series of tests.

SUMMARY OF THE INVENTION

It is an object of the present invention to provide improved dry, water-soluble, reagent formulations for use in conducting clinical diagnostic tests. It is a further object of the present invention to provide such formulations which can be readily granulated and shipped or stored in granular form. It is a particular object of the invention to provide such reagent formulations in free-flowing, granular form at consistent bulk densities so that they may be delivered to a volumetric packaging or tableting operation in consistent weight amounts. Additional objects of the invention include the provision of dry reagent formulations having a high capacity for solubilizing protein; the provision of such formulations having a high degree of storage stability; the provision of methods for preparing the dry reagent formulations of the invention; and the provision of methods for conducting clinical diagnostic tests utilizing such reagent formulations. Other objects and features will be in part apparent and in part pointed out hereinafter.

In one of its aspects, therefore, the present invention is directed to a reagent formulation for use in conducting a clinical diagnostic test on a biological specimen. The reagent formulation comprises a solid, water-soluble, substantially anhydrous, storage-stable mixture containing a reagent capable of participating in a test reaction to effect a measurable change in a test system, and a solid nitrogen-containing polyoxyalkylene nonionic surfactant. The surfactant has a structure corresponding to that obtained when ethylene diamine is reacted sequentially with propylene oxide and ethylene oxide in the presence of a catalyst and the polyoxypropylene chains of the surfactant have an average molecular weight of between about 750 and about 6750.

The invention is further directed to a method of conducting a clinical diagnostic test on a biological specimen using the aforementioned reagent formulation. The method comprises dissolving the reagent formulation in water to produce a liquid reagent; mixing the liquid reagent with a specimen to form a specimen/reagent test system; and measuring a change in the system resulting from the reaction between the reagent and the specimen.

The invention is also directed to a method of preparing the novel reagent formulation. The method comprises the steps of mixing a reagent capable of participating in a test reaction to effect a measurable change in a test system, a nitrogen-containing polyoxyalkylene nonionic surfactant of the above-noted character, and a solvent for the surfactant; and removing the solvent to form a substantially anhydrous, water-soluble, free-flowing, granular solid.

DESCRIPTION OF THE DRAWING

The drawing is a grid illustrating the molecular structure of various commercially available nonionic surfactants useful in the practice of the invention. The coordinates of each point on the grid correspond to the chain size of the polyoxyethylene hydrophile and polyoxypropylene hydrophobe moieties of a particular surfactant. Boundary lines set out on the grid separate the areas encompassing surfactants which assume different physical states.

DESCRIPTION OF THE PREFERRED EMBODIMENTS

To facilitate preparation of liquid reagents from solid formulations in the clinical laboratory, it is highly desirable to package the solid formulations in proper unitary amounts. Thus, for example, the solid formulations may be encapsulated or tabletted with the proper quantity of reagent in each capsule or tablet for conducting a single test. Alternatively, a multitest package can be provided from which the proper amount of liquid reagent is prepared for conducting a specified number of tests.

Where a solid reagent formulation is packaged in unitary amounts, accuracy of metering the solid material into each capsule, tablet or multi-test package is important. The metering equipment which is used for delivering solid materials in packaging and tableting operations, however, almost universally operates on a volumetric basis. Unless the solid material is free-flowing and has a consistent bulk density, therefore, it cannot be delivered in consistent weight amounts to each package, capsule or tableting station using conventional equipment.

To provide a solid formulation in free-flowing form of consistent bulk density, it is preferably granulated prior to packaging. Granulation converts a powdered material into a material constituted by small agglomerates of relatively uniform size. Properly prepared, the granular material is free-flowing, has a consistent bulk density and is readily handled by the metering devices used in packaging operations. To granulate a powdered material, the powder is typically mixed with a binder dissolved in a volatile solvent, wet screened, dried by driving off the solvent, and dry screened following the drying step. In addition to the binder, a lubricating substance is normally incorporated in the granulation mass to further enhance the flow characteristics of the granules, especially under the compressive stress of tableting operations.

As noted, solid formulations useful as reagents for conducting clinical diagnostic tests on biological specimens should have certain additional properties. Because they are dissolved in water to produce a liquid reagent, all components, including the binder, should be readily water-soluble. Because many of the tests involve enzymatic reactions and/or proteinaceous substrates, the formulation should possess detergent properties for solubilizing protein.

It has now been discovered that the above objectives can be met and that effective clinical reagent formulations for the determination of certain biological properties of body fluids can be produced in free-flowing, granular form through the use of particular nitrogen-bearing polyoxyalkylene nonionic surfactants. Test formulations granulated with the aid of these surfactants are well adapted to precision packaging and tableting operations. Because of their free-flowing character and consistent bulk density, they can be delivered to either a packaging or tableting operation in consistent weight amounts by volumetric metering. As a consequence, clinical test reagents formulated at a central location remote from a clinical laboratory can be utilized to prepare liquid test reagents for clinical use without the need for weighing, analyzing, or other procedures by the clinical chemist or technician.

The nitrogen-containing surfactants which are useful in the formulations of the invention possess the unique multiple capability of serving as binders, lubricants and solubilizers for protein. Moreover, they are themselves water-soluble, thus promoting the dissolution of the reagent formulations in water to provide clinical liquid reagents. These surfactants are sold under the trade designation "Tetronic" by Wyandotte Chemical Corporation. They are normally prepared by sequential reaction of first propylene oxide and then ethylene oxide with ethylene diamine in the presence of an alkaline or acid catalyst. Normally these surfactants are prepared at elevated temperatures using alkaline catalysts such as sodium hydroxide, potassium hydroxide, sodium alkoxide, quaternary ammonium bases and the like. Other methods are available for the preparation of these surfactants. The preparation of surfactants such as those utilized in the formulations of the invention is more fully described in U.S. Pat. No. 2,979,528.

The properties and physical state of nonionic surfactants having structures corresponding to those derived from ethylene diamine, propylene oxide and ethylene oxide vary with the lengths of the polyoxypropylene and polyoxyethylene chains. As the drawing shows, the physical state of these surfactants is largely dependent upon the proportionate weight of the surfactant constituted by the polyoxyethylene chains, but is also influenced by the average molecular weight of the polyoxypropylene moieties. The polyoxypropylene chains are hydrophobic while the polyoxyethylene chains are hydrophilic. Thus, the surfactants having polyoxypropylene units of low average molecular weight are more water-soluble than those having polyoxypropylene units of a higher average molecular weight. The numbers set out on the face of the grid correspond to particular members of the Tetronic series. Each number is located at a point on the grid whose coordinate correspond to the polyoxyethylene and polyoxypropylene chain sizes of the particular product which is commercially designated by said number.

Essentially any surfactant whose structure is defined by the coordinants of a point lying in the grid of the drawing may be utilized in the formulations of the invention. It is preferred, however, that the surfactant be solid or at least semi-solid. A greater proportion of the solid surfactants can be satisfactorily incorporated in a reagent formulation and thus a greater binding and lubricating capacity is obtained without adversely affecting other properties of the formulation. Desirably, on the order of 2.5 to 5% by weight of the preferred solid surfactants are incorporated in the reagent formulations. When the liquid formulations are used, it is not always possible to incorporate more than 2 or 3% by weight of the surfactant without imparting a somewhat waxy character to the formulation. The use of 2 to 3% by weight of a liquid "Tetronic" surfactant produces a useful product, but the binding and lubricating capabilities of the surfactant are not always fully exploited at such a level. Granules having the most desirable properties are obtained using solid or semi-solid surfactants.

Since the dry reagent formulations of the invention are dissolved in water for use in conducting clinical diagnostic tests, it is also desirable that the surfactant component promote the dissolution of the granular product. Thus, it is preferred that the surfactant be as hydrophilic as possible, i.e., that the molecular weight of the polyoxypropylene hydrophobe moiety of the surfactant be relatively low. Thus, the preferred surfactants for use in the formulations of the invention are those which are both solid or semisolid in physical state and relatively hydrophilic. Solid-state surfactants with polyoxypropylene chains having an average molecular weight of less than about 4000 are especially preferred, with the most suitable surfactants being those whose polyoxypropylene chains have an average molecular weight of between about 2750 and about 3750 and whose weight percentage of polyoxyethylene units is between about 70% and about 80%. Two particular surfactants whose weight and structure characteristics fall within the latter limits are those sold under the trade designations "Tetronic 707" and "Tetronic 908". "Tetronic 707" has a polyoxypropylene hydrophobe molecular weight on the order of 2750 and a weight percentage of polyoxyethylene units of about 70% while "Tetronic 908" has a polyoxypropylene molecular weight of about 3750 and a weight percentage of polyoxyethylene units of about 80%. Good results are also obtained with surfactants whose polyoxypropylene chains have an average molecular weight of between 750 and 4000 with a weight percentage of between about 35% and about 65% polyoxyethylene units. Other surfactants within the grid of the drawing are reasonably satisfactory but less effective than those represented by the right lower corner of the grid.

In addition to their advantageous effect upon granulation and dissolution of dry clinical test reagent formulations, surfactants of the above-noted character have been found to be effective for solubilizing protein. As indicated above, this is a highly advantageous characteristic, since enzymes and other proteinaceous matter derived from either the reagent formulation or the specimen commonly participate in the test reactions. By solubilizing protein, the surfactants function to facilitate the progress of the test reaction and thus enhance the effectiveness of the reagent formulation. It may, therefore, be seen that incorporation of these surfactants in clinical test formulations uniquely provides multiple advantages in the preparation, packaging, dissolution and functional operation of clinical reagent formulations.

It has further been discovered that the dry clinical reagent formulations of the invention are quite stable and generally possess good shelf life characteristics. Although we cannot precisely account for the particular ingredient or combination of ingredients which imparts the high degree of storage stability, it appears that such stability may be a somewhat general characteristic of dry clinical reagent formulations which include the particular nitrogen-containing nonionic surfactants used in our formulations. If so, the ability to impart storage-stability represents a further aspect of the unique multiple function of this type of surfactant in such formulations.

To prepare the reagent formulations of the invention, the surfactant is mixed with a volatile solvent and at least one reagent capable of participating in a test reaction to effect a measurable change in a reagent/sepcimen test system. The surfactant should be soluble up to the amount present in the solvent which is utilized. Solvents which may be used include methylene chloride, chloroform, methanol, benzene, water, methanol/water, and chloroform/methylene chloride. After thorough mixing and appropriate size classification, the solvent is removed to yield a granular product.

In a preferred embodiment of the invention, the ingredients of the formulation, in dry particulate form, are thoroughly blended in a mechanical mixer. With the mixer running, a granulating solution containing the solvent and the surfactant, preferably that sold under the trade designation "Tetronic 707" or "Tetronic 908", is added. Additional solvent is used as needed to produce granular agglomerates of the desired size and wetness.

The resulting wet granulation is screened through a coarse screen, for example 10 mesh, then spread in thin layers in trays and dried at reduced pressure, for example, 25 inch Hg absolute or less. Depending on the heat sensitivity of the formulation, drying is normally carried out at room temperature or at modest elevated temperature (up to about 37°C.). Generally, the depth of the wet granules in the trays should not exceed about ½ inch to ¾ inch.

After completion of the drying cycle, the dried granulation is rescreened through a finer screen, for example, 20 to 30 mesh, blended thoroughly and packaged in containers essentially impervious to moisture. Since the components of the reagent formulation are frequently moisture sensitive, the formulation should not be exposed to a relative humidity of more than about 5% after removal from the dryer.

The reagent formulations of the invention are adapted to be packaged in small unitary packages. For example, sufficient reagent formulation for a single assay may be tabletted or packaged in a capsule. The reagent formulations are also adapted to packaging in such containers as foil strip packets, utilizing automatic packaging machinery. Utilizing this package approach, sufficient reagent formulation to carry out a suitable predetermined number of tests, such as 10, 25, or 50 tests, may be accurately packaged in a single foil packet. The user then simply dissolves the contents of the multiple test packet in a predetermined volume of water and uses a suitable aliquot of the resulting liquid reagent in the performance of each of a series of assays for the desired biological substance or property.

In some instances, depending on the nature of the components and their compatibility, all of the reagents necessary in a single assay or determination may be included in a single formulation. In other instances, incompatabilities and/or other considerations may make it desirable to segregate certain reagents in which case two or more reagent formulations are prepared in accordance with the invention.

To conduct a clinical diagnostic test using the formulations of the invention, the liquid reagent produced by dissolving the dry formulation in a predetermined amount of water is mixed with the biological specimen in a predetermined volumetric or weight ratio. With the aid of appropriate instrumentation as required, the resulting specimen/reagent system is observed for the presence, absence, nature and extent of a physical, chemical or biological change. Such change as does occur is measured to provide the desired information for use in the clinical diagnosis.

Exemplary reagent formulations prepared in accordance with the invention and useful for the determination of hemoglobin, blood urea nitrogen, total protein, serum glutamic oxaloacetic transaminase, alkaline phosphatase, glucose, inorganic phosphorus, lactate dehydrogenase-L, serum glutamic pyruvic transaminase, uric acid (colorimetric) and uric acid (u.v.) are set forth in Table 1. The preferred compositions of these reagent formulations and methods for preparing them are described in the examples following Table 1 which more fully illustrate the invention.

Table 1

Exemplary Clinical Test Reagent Formulations

| Formulation | Type of Formulation | Dry Ingredients (Reagents, Etc.) Name/Formula | Wt. (g.) | Granulating Solution TETRONIC 707 (g.) | Polyethylene glycol 6000 (g.) | $CH_2Cl_2$ (ml.)[1] | Theoretical Yield (g.) | No. of Tests (Thousands) |
|---|---|---|---|---|---|---|---|---|
| A | Reagent Formulation for Hemoglobin Assay | $NaHCO_3$<br>$K_3Fe(CN)_6$<br>KCN<br>Mannitol | 300<br>50<br>30<br>590 | 30 | | (a) 200<br>(b) 300 | 1000 | 50 |
| B | Alkaline Chlorine Reagent Formulation for BUN Assay | Sodium Dichloroisocyanurate<br>LiOH<br>Mannitol | 120<br>240<br>180 | 15 | | (a) 200<br>(b) 100 | 555 | 30 |
| C | Chromogenic Reagent Formulation for BUN Assay | Sodium Salicylate<br>Sodium Nitroferricyanide | 1200<br>4 | 44 | 2 | (a) 250<br>(b) 100 | 1250 | 10 |
| D | Granular Enzyme Formulation for BUN Assay | Urease/EDTA Formulation (36,000 I.U.)<br>Mannitol | <br>579 | 15 | 6 | (a) 100<br>(b) 200 | 600 | 30 |
| E | Reagent Formulation for Total Protein Assay | Cupric Tartrate (Anhydrous)<br>Sodium Tartrate ($2H_2O$)<br>LiOH<br>RENEX-35 | 500<br>750<br>2000<br>500 | 100 | | (a) 1500<br>(b) 250 | 3850 | 50 |
| F | Coenzyme Formulation for GOT Assay | L-Aspartic Acid<br>MDH Formulation (containing 6.0 mg. MDH; 1.4 I.U.)<br>NADH Formulation (containing 0.5 mg. NADH)<br>Tris-(hydroxymethyl)-aminomethane<br>Succinic Acid | 1250<br><br><br><br>1875<br>187.5 | 80 | | (a) 800<br>(b) 525 | | 25 |
| G | Substrate Formulation for GOT Assay | Sodium Alpha-Ketoglutarate<br>Mannitol | 200<br>765 | 25 | | (a) 500<br>(b) 200 | 990 | 50 |
| H | Reducer Formulation for Alkaline Phosphatase Assay | Ascorbic Acid<br>Sulfamic Acid | 3250<br>1600 | 150 | | (a) 500<br>(b) 200 | 5000 | 50 |
| I | Molybdate Formulation for Alkaline Phosphatase Assay | Sodium Molybdate (<2% $H_2O$)<br>Duponol ME Dry | 475<br>737.5 | 37.5 | | (a) 300<br>(b) 150 | 1250 | 50 |
| J | Substrate Formulation for Alkaline Phosphatase Assay | Disodium β-Glycerophosphate<br>Tris-(hydroxymethyl)-aminomethane<br>Succinic Acid<br>Duponol ME Dry | 500<br>1500<br>12.5<br>500 | 87.5 | | (a) 400<br>(b) 100 | 2600 | 50 |
| K | Chromogen Formulation for Glucose Assay | O-Dianisidine.2HCl<br>Mannitol | 7.5<br>423.6 | 14.4 | 4.5 | (a) 150<br>(b) 125 | | 30 |
| L | Buffer Formulation for Glucose Assay | $NaH_2PO_4 \cdot H_2O$<br>$Na_2HPO_4$<br>Mannitol<br>Spray Dried Gum Arabic | 311.4<br>190.8<br>52.8<br>30.0 | 15.0 | | (a) 40[2]<br>(b) 5–10[2] | 600 | 30 |
| M | Enzyme Formulation for Glucose Assay | Glucose Oxidase Stabilized<br>Mannitol<br>Horseradish Peroxidase<br>Mannitol | 420<br><br>30<br> | 15.0 | 3.0 | (a) 40[2]<br>(b) 10[2] | 450 | 30 |
| N | Reducer Formulation for Inorganic Phosphorus Assay | Ascorbic Acid<br>Sulfamic Acid<br>Duponol ME Dry | 3250<br>800<br>775 | 125 | | (a) 1000<br>(b) 500 | 4950 | 50 |
| O | Molybdate Formulation for Inorganic Phosphorus Assay | Tris-(hydroxymethyl)-aminomethane<br>Duponol ME Dry<br>Sodium Molybdate (<2% $H_2O$) | 1500<br>470<br>950 | 80 | | (a) 475<br>(b) 175 | 3000 | 100 |
| P | Coenzyme Formulation for Lactate Dehydrogenase Assay | NAD Modified (=225 g NAD)<br>Mannitol | 1190 | 60 | | (a) 500<br>(b) 250 | 1250 | 50 |

Table 1-continued

Exemplary Clinical Test Reagent Formulations

| Formulation | Type of Formulation | Dry Ingredients (Reagents, Etc.) Name/Formula | Wt. (g.) | TETRONIC 707 (g.) | Granulating Solution Polyethylene glycol 6000 (g.) | CH$_2$Cl$_2$ (ml.)[1] | Theoretical Yield (g.) | No. of Tests (Thousands) |
|---|---|---|---|---|---|---|---|---|
| Q | Substrate Formulation for Lactate Dehydrogenase Assay | Lithium Lactate | 2250 | 75 | 25 | (a) 500 | 3200 | 50 |
|  |  | Tris-(hydroxymethyl)-aminomethane | 225 |  |  | (b) 1175 |  |  |
|  |  | NaHCO$_3$ | 450 |  |  |  |  |  |
|  |  | Renex 35 | 175 |  |  |  |  |  |
| R | Coenzyme Formulation for Serum Glutamic Pyruvic Transaminase Assay | NADH Formulation (equivalent to 0.4 mg. NADH) |  |  |  |  |  |  |
|  |  | LDH Formulation (equivalent to 2 units LDH) |  |  |  |  |  |  |
|  |  | DL-Alanine | 1200 | 50.4 |  | (a) 200 |  | 15 |
|  |  | Sodium phosphate, dibasic | 585 |  |  | (b) 70 |  |  |
|  |  | Sodium phosphate, monobasic | 75 |  |  |  |  |  |
| S | Substrate Formulation for Serum Glutamic Pyruvic Transaminase Assay | (See Formulation G Above) |  |  |  |  |  |  |
| T | Enzyme Formulation for Uric Acid Assay | Uricase Formulation (equivalent to 0.05 units) |  |  |  |  |  |  |
|  |  | Glycine | 113.25 | 4.50 |  | (a) 25 |  | 7.5 |
|  |  | Sodium carbonate, anhydrous | 39.75 |  |  | (b) 10 |  |  |
| U | Copper Reagent Formulation for Uric Acid Assay | Tris-(hydroxymethyl)-aminomethane | 112.50 | 7.05 |  | (a) 15 | 234 | 7.5 |
|  |  | Sodium bicarbonate | 112.50 |  |  | (b) 5 |  |  |
|  |  | Copper Sulfate, anhydrous | 1.95 |  |  |  |  |  |
| V | Neocuproine Formulation for Uric Acid Assay | Neocuproine . HCl | 5.25 | 4.75 |  | (a) 30 | 160 | 7.5 |
|  |  | Renex 35 | 150 |  |  | (b) 10 |  |  |
| W | Blank Formulation for Uric Acid Assay | Uricase Placebo | 19.50 | 4.50 |  | (a) 25 | 177 | 7.5 |
|  |  | Glycine | 113.25 |  |  | (b) 10 |  |  |
|  |  | Sodium carbonate, anhydrous | 39.75 |  |  |  |  |  |

[1](a) indicates amount of CH$_2$Cl$_2$ used as carrier for Tetronic 707
(b) indicates amount of additional CH$_2$Cl$_2$ used to optimize granulation
[2]solvent is water instead of CH$_2$Cl$_2$

EXAMPLE 1

Hemoglobin Reagent Formulation and Assay

Composition of the reagent formulation useful for hemoglobin assay is set forth as formulation A in Table 1.

To prepare this formulation, sodium bicarbonate (300 g.), milled potassium ferricyanide (50 g.) and potassium cyanide (30 g.) were initially added to a Hobart bowl and mixed with a stainless steel spatula. Mannitol (590 g.) was then added and the resulting blend was agitated for 5 minutes in the mixer. While agitation was continued, a solution of "Tetronic 707" (30 g.) in methylene chloride (200 ml.) was added. An additional amount of methylene chloride (300 ml.) was then added to produce the proper granulation.

The wet granulation was screened through a No. 10 mesh stainless steel screen and the wet screened material was transferred to 8 inch × 12 inch Pyrex drying trays, at a depth of between about ½ inch and about ¾ inches in each tray. The granulation was then dried in a vacuum oven for 15 hours at a temperature of 35°C. and a pressure of 25 inch Hg.

The dried granulation was removed from the vacuum oven in an environment where the relative humidity was not more than 5%. The dried granulation was then screened through a No. 20 mesh stainless steel screen using an Erweka oscillator. The screened, dried granulation was transferred to a P.K. blender and mixed for 5 minutes, then packaged in tightly closed containers. Approximately 1000 g. of a water-soluble, substantially anhydrous reagent formulation, sufficient for 50,000 tests, was obtained.

Upon being stored at a temperature of 45°C., the above-prepared formulation was found to be stable for at least 23 weeks which is equivalent to a stability period of 92 weeks at room temperature.

Dissolved in water, formulation A yields a liquid reagent useful in assaying blood hemoglobin. By action of the dissolved reagent, erythrocytes in the blood are hemolyzed releasing hemoglobin which is oxidized to methemoglobin. Methemoglobin is converted to cyanmethemoglobin whose formation alters the optical density of the reagent/specimen system. The optical density of the reagent/specimen system is measured at 540 nm. using a suitable spectrophotometer and compared against a reagent blank set at 100% transmission. The hemoglobin level is then determined by reference to a standard curve.

To prepare a liquid reagent sufficient for 50 tests, formulation A (1.00 g.) is dissolved in distilled water and the resulting solution is diluted to 250 ml. and mixed thoroughly. The reagent solution thus produced is stable for three months at room temperature if protected from light.

To conduct the hemoglobin assay test, a reagent/specimen test system is prepared by adding 20 microliters of well mixed blood (collected with an anticoagulant) to 5 ml. of the above solution of formulation A in a clean test tube. The contents of the tube are mixed thoroughly and allowed to stand at room temperature for at least 5 minutes. The optical density is then measured as described above to determine the hemoglobin level.

EXAMPLE 2

Blood Urea Nitrogen Formulations and Assay

Because certain components of the total number of reagents required for a blood urea nitrogen (BUN) test tend to interact with one another in the dry state, three separate formulations are provided to segregate the interacting components. The three formulations prepared are set forth in Table 1 as formulations B, C and D. Predetermined amounts of each of these formulations are dissolved in separate portions of water to provide liquid reagents for use in making the BUN assay.

To prepare alkaline chlorine reagent formulation B, sodium dichloroisocyanurate, sold under the trade designation "ACL-60" by Monsanto Co. (120 g.), anhydrous lithium hydroxide (240 g.), and mannitol powder (180 g.) were blended in a Hobart bowl and agitated to promote intimate mixing. With the mixer running, a solution of "Tetronic 707" (15 g.) in methylene chloride (200 ml.) was introduced. Additional methylene chloride (100 ml.) was subsequently added to produce the desired degree of granulation and wetness. The wet granulation was screened and dried, and the resultant dry granulation rescreened and packaged, in the manner described in Example 1 for hemoglobin reagent formulation A.

In the preparation of the chromogenic reagent formulation C, sodium salicylate (1200 g.) and sodium nitroferricyanide (4 g.) were blended in a Hobart bowl and agitated to promote intimate mixing. With the mixer running, a solution of "Tetronic 707" (44 g.) and polyethylene glycol having a molecular weight of about 6000 (2 g.) in methylene chloride (250 ml.) was added. Additional methylene chloride (approximately 100 ml.) was subsequently introduced to produce the desired degree of granulation. The wet granulation was screened and dried, and the resultant dry granulation rescreened and packaged, as described in Example 1 for hemoglobin reagent formulation A.

Before blending the constituents of granular enzyme formulation D, the lyophilized urease/ethylenediaminetetraacetic acid (EDTA) component was prepared. To prepare this component disodium EDTA (24 g.) and tetrasodium EDTA (15.12 g.) were dissolved in distilled water (about 900 ml.) with heating as required. A carbohydrate polymer having a number average molecular weight of about 1850, a dextrose equivalent of 10–13, a pH of 4.5–5.5, and a decomposition point of 440°F., sold under the trade designation "Amisol" by Corn Products Company (11 g.) was added and the solution was cooled to about 4°C. Lyophilized urease powder having a specific activity of approximately 200 IU/mg., such as that sold by Worthington Biochemical Corporation, Code No. URPC, (100,000 International Units) was dissolved in this solution. The solution was filtered through glass wool or cotton to remove any turbidity. The clarified solution was divided and each portion placed in one of several freeze drying vessels and the portions frozen in thin layers by rotating the vessels in a dry ice/alcohol bath at −60°C. or below. The frozen thin layers were lyophilized at −60°C. to −70°C. at a total pressure of 5 m$\mu$Hg. for 16 to 24 hours. The resultant lyophilized powder was collected under an atmosphere having a relative humidity of less than 5% and stored in a desiccator at 4°C. Assay of the specific urease activity of the dried powder was in the range of 2 to 3 I.U./mg. at 37°C. It was found that the modified urease product thus produced is stable at room temperature and does not require refrigeration.

The following exemplary procedure provides approximately 600 grams of granular enzyme formulation containing 12 I.U. urease/20 mg. utilizing a lyophilized urease/EDTA formulation having a specific urease activity of 3.0 I.U./mg.

To prepare granular enzyme formulation D, lump-free mannitol (459 mg.) and the lyophilized urease/EDTA formulation prepared as above and having an activity of 3.0 I.U./mg. (120 g.) were blended in a Hobart bowl and agitated to promote intimate mixing. With the mixer running, a solution of "Tetronic 707" (15 g.) and polyethylene glycol having a molecular weight of about 6,000 (6 g.) in methylene chloride (100 ml.) was added to the blend. Additional methylene chloride (approximately 200 ml.) was subsequently introduced to produce the desired degree of granulation. The wet granulation was then screened and dried at room temperature, and the resulting dry granulation rescreened and packaged, in the manner described for hemoglobin reagent formulation A in Example 1.

Upon being stored at a temperature of 45°C. the above prepared formulations were found to be stable for at least 21 weeks which is equivalent to a stability period of 84 weeks at room temperature.

Dissolved in separate portions of water, formulations B, C and D provide liquid reagents useful in the determination of blood urea nitrogen. The urease of formulation D specifically hydrolyzes urea to ammonium carbonate, which is subsequently decomposed by the addition of the alkali in formulation B to produce carbon dioxide and ammonia. In the presence of the catalyst, sodium nitroferricyanide, of chromogenic reagent formulation C, ammonia reacts with the phenol derivative of formulation C and active chlorine from formulation B to form an emerald green color complex. The intensity of the color is measured colorimetrically at 650 nm. and is proportional to the urea present.

Preparatory to conducting the test, formulation B (0.925 g.), formulation C (6.25 g.) and formulation D (1.0 g.) are each dissolved in water in separate containers. The solution of formulation D is diluted to 50 ml. while the solutions of formulations B and C are each diluted to 25 ml. All of the diluted solutions are thoroughly mixed. The solution of formulation D is stable for one month under refrigeration. The solutions of formulations B and D are stable for 3 months if kept in amber bottles under refrigeration. The resulting solutions are sufficient for conducting 50 tests.

In the conduct of the test, 1.00 ml. of the dilute solution of formulation D and 0.005 ml. (5 lambda) of serum are placed in a test tube, mixed well and incubated at 37°C. for 5 minutes to effect enzymatic hydrolysis. Formulation C solution (0.5 ml.) is then added with careful mixing, immediately following which the solution of formulation B (0.50 ml.) is added and thoroughly mixed with the other components of the solution. Incubation is continued at 37°C. for an additional 10 minutes for color development. At the end of this period, distilled water (2.00 ml.) is added and the optical density at 650 nm. is read using a spectrophotometer and compared with the optical density of a reagent blank set at 100% transmission. The urea level in the specimen is then determined by reference to a standard curve.

EXAMPLE 3

Total Protein Formulation and Assay

The reagent formulation utilized in determination of total protein in a biological specimen is set forth as formulation E in Table 1.

In the preparation of formulation E, anhydrous cupric tartrate (500 g.), dihydrated sodium tartrate (750 g.), lithium hydroxide (2000 g.) and a surfactant comprising a polyoxyethylene ether alcohol and urea sold under the trade designation "Renex 35" by Atlas Chemical Industries (500 g.) were blended and thoroughly agitated in a Hobart bowl mixer. With the mixer running, a solution of "Tetronic 707" (100 g.) in methylene chloride (1500 ml.) was added. Additional methylene cloride (250 ml.) was then introduced to produce the desired degree of granulation and wetness. The wet granulation was screened and dried and the resultant dried granulation rescreened and packaged in the manner described in Example 1 for hemoglobin reagent formulation A.

Upon being stored at a temperature of 45°C., the above-prepared formulation was found to be stable for at least four weeks which is equivalent to a stability period of 16 weeks at room temperature.

Dissolved in water, formulation E yields a liquid reagent useful in assaying a body fluid for total protein. The biuret reaction of proteins with the alkaline cupric tartrate constituent of formulation E results in the formulation of a violet color.

To prepare the liquid reagent, formulation E (1.925 g.) is dissolved in distilled water and the solution is diluted to 100 ml. and thoroughly mixed. This reagent solution is stable for at least three months at room temperature, and is sufficient to conduct 25 tests.

In the conduct of the total protein test, a reagent/specimen assay system is prepared by adding 50 microliters of serum to 4.0 ml. of the solution of formulation E in a test tube. The contents of the tube are mixed thoroughly and incubated at 37°C. for 15 minutes. The optical density at 540 nm. is then read using a spectrophotometer and compared with a reagent blank set at 100% transmission. The total protein level is then determined by reference to a standard curve.

EXAMPLE 4

Serum Glutamic Oxaloacetic Transaminase Formulations and Assay

For the serum glutamic oxaloacetic transaminase (SGOT) test, two separate formulations are provided. The two formulations which are utilized are set forth in Table 1 as formulations F and G. Predetermined amounts of these formulations are dissolved in separate portions of water to provide liquid reagents for use in making the SGOT assay.

Preparatory to blending the constituents of coenzyme formulation F, the modified malate dehydrogenase and reduced nicotinamide adenine dinucleotide components are prepared.

Modified malate dehydrogenase was derived from yellow split peas. The peas were pulverized to a fine powder using a mill or a micromill. A saturated solution of potassium chloride was prepared at room temperature by stirring potassium chloride (500 g.) in approximately 1 l. of distilled water for 5 minutes and allowing the solution to stand at room temperature overnight. Pulverized pea powder (10 g.) was stirred into a 50 ml. portion of the unsaturated potassium chloride solution, which extracted the malate dehydrogenase therefrom. Extraction was carried out at room temperature for approximately 3 hours with occasional stirring. At the end of the 3 hour extraction period, the resulting suspension was centrifuged at 10,000 rpm using a No. 872 angle rotor in an IEC B–20 refrigerated centrifuge at 10°C. for 10 minutes. The slightly colloidal supernatant extract fluid was collected and transferred to a plurality of freeze drying vessels. The extract was frozen in thin layers by rotating each vessel in a dry ice/alcohol bath at −60°C. or below. The frozen thin layers were lyophilized at −60°C. to −70°C. and an absolute pressure of 5m$\mu$Hg for 18 to 20 hours. The resultant lyophilized powder was collected under an atmosphere having a relative humidity of less than 5% and stored in a dessicator at 4°C. Approximately 14 g. of dry powder was obtained which was assayed for the enzymic activities of both malate dehydrogenase (MDH) and glutamic oxaloacetic transaminase (GOT). GOT specific activity was less than about 0.05% in relation to MDH specific activity, and the extract enzyme was, therefore, suitable for use. Activity of the MDH obtained was about 1.4 I.U./6 mg.

To prepare modified reduced nicotinamide adenine dinucleotide (NADH), gum arabic (15 g.), tris-(hydroxymethyl)-aminomethane (12 g.), "Amisol" (10 g.), and bovine serum albumin (0.5 g.) were dissolved in distilled water (450 ml.) and the resulting solution was titrated to pH 9.0 with 12N sulfuric acid. After titration, the solution was diluted to 500 milliliters with distilled water and clarified by centrifugation at 10,000 rmp with a No. 872 angle rotor in an IEC B-20 refrigerated centrifuge at 10°C. for 16 minutes. To the supernatant obtained from this centrifugation, 10 g. of NADH powder (reduced nicotinamide adenine dinucleotide disodium salt) was added and the resulting mixture stirred for at least 5 minutes to insure good mixing. This mixture was transferred into freeze drying vessels and frozen in thin layers by rotating the vessels in a dry ice/alcohol bath at −60°C. or below. The frozen thin layers were lyophilized for 20 to 24 hours at −60°C. to −70°C. and an absolute pressure of 5 m$\mu$Hg. The resultant lyophilized powder was collected under an atmosphere having a relative humidity of less than 5% and stored in a dessicator at 4°C. Approximately 50 g. of dry lyophilized powder was obtained.

To prepare coenzyme formulation F L-aspartic acid (1250 g.), the above modified MDH (equivalent to 1.4 0 I.U. or 6.0 milligrams MDH), the above modified NADH (equivalent to 0.5 milligrams NADH), tris-(hydroxymethyl)-aminoethane (1875 g.), and milled succinic acid (187.5 g.) were blended in a Hobart bowl mixer and agitated to promote intimate mixing. With the mixer running, a solution of "Tetronic 707" (25 g.) in methylene chloride (800 ml.) was added to the blend. Additional methylene chloride (approximately 525 ml.) was subsequently introduced to produce the desired degree of granulation and wetness. The wet granulation was then screened and dried at room temperature, and the resulting dry granulation rescreened and packaged, in the manner described for hemoglobin reagent formulation A in Example 1.

To prepare substrate formulation G, sodium α-ketoglutarate (200 g.) and lump-free mannitol (765 M.) were blended in a Hobart bowl and agitated to promote intimate mixing. With the mixer running, a solution of "Tetronic 707" (25 g.) in methylene chloride (500 ml.) was added to the blend. Additional methylene chloride (approximately 200 ml.) was subsequently introduced to produce the desired degree of granulation and wetness. The Wet granulation was then screened and dried at room temperature and 25 inches pressure or less and the resulting dry granulation rescreened and packaged, in the manner described for hemoglobin reagent formulation A in Example 1.

Upon being stored at a temperature of 45°C., the above-prepared formulations were found to be stable for at least 3 weeks which is equivalent to a stability period of 12 weeks at room temperature.

Dissolved in separate portions of water, formulations F and G provide liguid reagents useful in assaying for serum glutamic oxaloacetic transaminase. SGOT present in the specimen catalyzes the transamination of L-aspartic acid and α-ketoglutaric acid producing oxaloacetate and glutamate. The oxaloacetate and NADH in the presence of MDH are converted to malate and NAD. The extent of reaction is indicative of the SGOT present and is measured by observing a decrease in optical density at 340 nm. at 37 °C.

The liquid reagent solution of formulation F is prepared by dissolving 7.2 g. of the formulation in distilled water, diluting to 125 ml. and mixing well. The solution of formulation G is prepared in similar fashion utilizing a 1.0 g. of the formulation and diluting to 25 ml. The formulation F solution should be prepared fresh daily while the formulation G solution is stable for a week under refrigeration.

In the conduct of the test, 2.5 ml. of the formulation F solution are placed in a test tube, 0.1 ml. of serum are added thereto, and the resulting solution stirred and incubated at 37°C. in a heating unit for 7 to 10 minutes. 0.5 ml. of the formulation G solution is then added and mixed quickly in less than 10 seconds at room temperature. Exactly 2 minutes after the liquid reagent solution of formulation G is added, the test tube is removed from the heating unit and the absorbance of the reagent/specimen system is measured. The tube is then returned to the heating unit and held there until exactly 5 minutes after the solution of formulation G was first added. At this point, the tube is again removed from the heating unit and the final absorbance of the reagent/specimen system is measured. The SGOT content is determined from the two absorbance readings by calculation utilizing the following equation:

$$\frac{A_1 - A_2}{L} \times 1667 = \text{SGOT units/ml. serum}$$

where $A_1$ equals absorbance read at 2 minutes, $A_2$ absorbance read at 5 minutes, L equals light path of the absorption cell or the I.D. of the test tube in centimeters. An SGOT unit is defined as that amount of enzyme which catalyzes the oxidation of 0.001 micromole of NADH to NAD per minute, at 37°C. Other conditions for determining SGOT are known. The Karmen procedure known to the art carries out the above reactions at 25°C. instead of 37°C.

EXAMPLE 5

Alkaline Phosphatase Formulations and Assay

Three separate formulations are provided for the alkaline phosphatase test. These formulations are set forth in Table 1 as formulations H, I and J. Predetermined amounts of these formulations dissolved in separate portions of water provided liquid reagents for use in making the alkaline phosphatase assay.

Prior to the preparation of chromogenic reagent formulation I, the sodium molybdate component of the reagent blend was dried. Sodium molybdate was transferred into tared 8 inch × 12 inch Pyrex trays at a depth of between about ½ inch and ¾ inch. The trays were then placed in a vacuum oven and the sodium molybdate dried at 55°C. and a total pressure of 25 inch Hg until a weight loss of not less than 13% was observed.

To prepare chromogenic reagent formulation I, the dried sodium molybdate (475 g.) and a dry sodium lauryl sulfate product sold under the trade designation "Duponol ME" by E. I. DuPont de Nemours and Company (737.5 g.) were blended in a Hobart bowl and agitated to promote intimate mixing. With the mixer running, a solution of "Tetronic 707" (37.5 g.) in methylene chloride (300 ml.) was introduced. Additional methylene chloride (150 ml.) was subsequently added to produce the desired degree of granulation and wetness. The wet granulation was screened and dried and the resultant dry granulation rescreened and packaged in the manner described in Example 1 for hemoglobin reagent formulation A.

In the preparation of reducer quench formulation H, L-ascorbic acid (3.25 kg.) and sulfamic acid (1.60 kg.) were blended in a Hobart bowl and agitated to promote intimate mixing. With the mixer running, a solution of "Tetronic 707" (150 g.) in methylene chloride (500 ml.) was introduced. Additional methylene chloride (200 ml.) was subsequently added to produce the desired degree of granulation and wetness. The wet granulation was screened and dried and the resultant dry granulation rescreened and packaged in the manner described in Example 1 for hemoglobin reagent formulation A.

Preparation of buffer substrate reagent formulation J was initiated by blending β-glycerophosphoric acid, disodium salt (500 g.) tris-(hydroxymethyl)-aminomethane (1.5 kg.), milled succinic acid (12.5 g.) and "Duponol ME" (500 g.) in a Hobart bowl and agitating the blend to promote intimate mixing. With the mixer running, a solution of "Tetronic 707" (87.5 g.) in methylene chloride (400 ml.) was introduced. Additional methylene chloride (100 ml.) was subsequently added to produce the desired degree of granulation and wetness. The wet granulation was screened and dried and the resultant dry granulation rescreened and packed in the manner described in Example 1 for hemoglobin reagent formulation A.

Dissolved in separate portions of water, formulations H, I and J provide liquid reagents useful in the determination of the alkaline phosphatase content of biological specimens such as blood serum. Alkaline phosphatase in the specimen promotes the release of phosphate from the β-glycerophosphate constituent of substrate reagent formulation J. The phosphate thus released reacts with sodium molybdate of chromogenic reagent formulation I in the presence of sulfamic acid and ascorbic acid of reducer quench formulation H. The ascorbic acid reduces the phosphomolybdic acid thus formed to phosphomolybdenum blue. The color of the latter is indicative of the concentration of alkaline phosphatase present in the reagent specimen system.

In preparation for a test, the dry reagent formulations are each dissolved in water to provide liquid reagents. Formulation I (1.25 g.) is dissolved in 25 ml. of distilled water to provide a chromogenic liquid reagent; formulation H (5.00 g.) is dissolved in 25 ml. of water to provide a reducer quench liquid reagent; and formulation J (2.60 g.) is dissolved in 150 ml. of water to provide a substrate buffer liquid reagent. The solution of formulation I is stable for a week at room temperature. The solution of formulation J is stable for two weeks when refrigerated. The liquid reagent constituted by the solution of formulation H should be prepared fresh daily and protected from light. The resulting solutions are sufficient for conducting 50 tests.

Conduct of an alkaline phosphatase determination is initiated by adding 3 ml. portions of the solution of substrate formulation J to each of two test tubes and incubating each tube for 2 minutes at 37+C. One of the two tubes is then used for the test reaction while the other tube is used for a blank.

0.1 ml. (100 lambda) of serum is added to the tube used for the test reaction and mixed thoroughly with the liquid reagent therein to provide a specimen/reagent test system. The test system is then incubated for exactly 15 minutes at 37°C., following which 0.5 ml. portions of the liquid reagent solution of formulation I and 0.5 ml. portions of the liquid reagent solution of formulation H are added to both the test system and the tube carrying the test blank. Both the test system and the blank are then incubated at 37°C. for another 20 minutes, and the optical density of each determined at 700 nm against a water blank set at 100% transmission. Using a standard curve, the inorganic phosphorus content of each test solution is determined from its optical density compared to the water blank. Since both the test system and test blank originally contain the same amount or proportion of β-glycerophosphate, the inorganic phosphorus released by action of alkaline phosphatase is determined by subtracting the total inorganic phosphorus in the test system from the total amount of inorganic phosphorus in the blank.

To calculate the alkaline phosphatase units present in the test system, the mg% inorganic phosphorus released in multiplied by 4. In the procedure of Bodansky, known to the art, there is one-to-one correspondence between the mg% phosphorus released and the alkaline phosphatase units. Since the test of the invention utilizes only a 15 minute incubation time instead of the 60 minute incubation time of Bodansky, the factor of 4 is applied to obtain corresponding results.

The standard curve used to determine absolute inorganic phosphorus is obtained by spectrophotometric measurements of the optical densities of potassium dihydrogen phosphate solutions containing 0, 2.5, 5.0, 7.5 and 10 mg% phosphorus at 700 nm, against a reagent blank set at 100% transmission. A standard potassium dihydrogen phosphate solution for use in establishing the standard curve is prepared by weighing out $KH_2PO_4$ (438.1 mg.) in a 100 ml. volumetric flask, diluting to volume with high quality distilled water, and storing the diluted solution at 4°C. This stock solution contains 100 mg. phosphorus per 100 ml. (100 mg%) and appropriately diluted aliquots of this stock solution are used in establishing the standard curve.

As those skilled in the art will appreciate, phosphorus standard curves obtained from spectrophotometric measurements of varying concentrations of potassium dihydrogen phosphate are linear only up to abot 15 mg%. Where high phosphorus sera (above 7.5 mg%) are analyzed for alkaline phosphatase content, therefore, a 50 lambda serum sample is used and the final result multiplied by 2.

An alkaline phosphatase unit is defined as the amount of enzyme in 100 ml. of serum which releases 1 mg. phosphorus per hour at 37°C.

EXAMPLE 6

Glucose Reagent Formulations and Assay

For the glucose test, three separate formulations are provided. These are set forth in Table 1 as formulations K, L and M. Predetermined amounts of these formulations are dissolved in separate portions of water to provide liquid reagents for use in making the glucose assay.

To prepare chromogenic reagent formulation K, mannitol (423.6 g.) and o-dianisidine dihydrochloride (3,3-dimethoxybenzidine dihydrochloride) (7.5 g.) were blended in a Hobart bowl and agitated to promote intimate mixing. With the mixer running, a solution of "Tetronic 707" (14.4 g.) and polyethylene glycol-6000 (4.5 g.) in methylene chloride (150 ml.) was introduced. Additional methylene chloride (125 ml.) was subsequently added to produce the desired degree of granulation and wetness. The wet granulation was screened and dried at room temperature, and the resultant dry granulation rescreened and packaged in the manner described in Example 1 for hemoglobin reagent formulation A.

Buffer reagent formulation L was prepared by blending monobasic sodium phosphate (311.4 g.), dibasic sodium phosphate (190.8 g.), mannitol (52.8 g.) and spray dried gum arabic (30.0 g.) in a Hobart bowl and agitating the resulting blend to promote intimate mixing. With the mixer running, a solution of "Tetronic 707" (15.0 g.) in distilled water (40 ml.) was introduced. Additional distilled water (1 m.) was subsequently added to produce the desired degree of granulation and wetness. The wet granulation was screened and dried and the resultant dry granulation rescreened and packaged in the manner described in Example 1 for hemoglobin reagent formulation A.

To prepare modified glucose oxidase, gum arabic (60 g.) and mannitol (40 g.) were dissolved in water (about 1600 ml.) and the resulting colloidal solution was titrated to pH 7.0 with 2% sodium hydroxide. After titration, the solution was diluted to 2 liters with distilled water and clarified by centrifugation at 10,000 rpm with a No. 872 angle rotor in an IEC B–20 refrigerated centrifuge. The clear supernatant inert solution was collected and stored at 4°C. Bovine serum albumin (2 g.) was dissolved in 200 ml. of the above prepared inert solution with the aid of a magnetic stirrer. Liquid glucose oxidase (200 ml.) having a specific activity greater than 1000 titrimetric units per ml. was then slowly added and the resulting mixture stirred for an additional 5 minutes to insure good mixing. This solution was transferred into freeze drying vessels, each vessel being filled with 150–200 ml. of the solution. The solution was frozen in thin layers by rotating the vessels in a dry ice/alcohol bath at −60°C. or below. The frozen layers were lyophilized for 16 to 20 hours at −60°C. to −70°C. and an absolute pressure of 5m μHg. The resultant lyophilized powder was collected under an atmosphere having a relative humidity of less than 5% and stored in a desicator at 4°C. Approximately 14 g. of dry lyophilized glucose oxidase powder with a specific activity range of 14–16 IU/mg. at 37°C. was obtained.

In the preparation of enzyme reagent formulation M, a glucose oxidase (GOD) subformulation was initially produced. The above modified glucose oxidase (sufficient to provide 45 units of unmodified material/test) and mannitol (sufficient to provide 14 mg. — total of modified GOD plus mannitol — per test) were blended in a Hobart bowl and thoroughly agitated to promote initimate mixing. With the mixer running, a solution of "Tetronic 707" (15.0 g.) and polyethylene glycol-6000 (3.0 g.) in distilled water (40 ml.) was introduced. Additional distilled water (10 ml.) was subsequently added to produce the desired degree of granulation and wetness. The wet granulation was screened and dried at room temperature, and the resultant dry granulation rescreened in the manner described in Example 1 for hemoglobin reagent formulation A. The dry, rescreened granulated glucose oxidase subformulation was transferred to a tared 1500 cc amber bottle and stored in a dry room pending subsequent intermixture with the other constituents of formulation M, as described below. Each gram of this granulated glucose oxidase subformulation contains sufficient GOD for the conduct of 71 glucose test. The yield of this formulation in terms of potential test; units maay therefore be calculated as follows:

No. of tests = wt. of GOD subformulation (g.) × 71 tests g.

A peroxidase trituration subformulation for formulation M was prepared by blending, with mortar and pestle, an amount of horseradish peroxidase (POD) and an amount of mannitor for the number of tests calculated above and determined by the following respective calculations:

$$POD(mg.) = No.\ of\ tests \times \frac{440\ units}{test} \times \frac{1}{K\ (units/mg.)}$$

$$mannitol\ (g.) = \left[ No.\ tests \times \frac{1.0\ mg.}{test} - \frac{mg.\ POD}{Test} \right] \times \frac{1\ g.}{1000\ mg.}$$

$$K\ \frac{units\ POD}{mg.\ POD}$$

being determined by prior assay.

To the trituration thus provide, 25 g. of the glucose oxidase subformulation was added and the resultant mixture agitated with a stainless steel spatula to disperse the trituration.

After preparation of the GOD/POD dispersion 50 g. of the GOD subformulation, the dispersion, and an additional 50 g. of the GOD subformulation, were sequentially screened through a 40 mesh stainless steel screen onto a clean receiving surface. All of the screened material was then transferred to a PK blender, along with the remainder of the GOD subformulation, and mixed for more than 5 minutes. The resultant blended granulation was transferred into 8 inch × 12 inch Pyrex trays at a depth of ½ inch or ¾ inch and dried for about 15 hours at room temperature and a total pressure of 25 inch Hg.

Dissolved in two separate portions of water, formulation K, and formulation L together with M, provide liquid reagent solutions useful in the determination of true glucose in a biological specimen such as blood serum. In the presence of water and the glucose oxidase component of enzyme formulation M, glucose in the specimen is oxidized to gluconic acid with hydrogen peroxide formed as a product. The by product, hydrogen peroxide, oxidizes the o-dianisidine constituent of chromogenic reagent formulation K, in the presence of horseradish peroxidase, producing a colored product which causes an increase in optical density at 445 nm. The extent of the increase indicates the concentration of glucose in the test system.

A chromogenic liquid reagent is prepared by dissolving formulation K (0.75 g.) in 50 ml. water. A liquid reagent having both enzyme activity and buffering capacity is prepared by dissolving formulation M (0.75 g.) and formulation L (1.0 g.) in another 50 ml. portion of distilled water. The chromogenic liquid reagent should be prepared fresh daily. The liquid reagent containing formulations L and M is stable for at least 1 week if refrigerated. The resulting solutions are sufficient for conducting 50 tests.

In the conduct of the test, 1 ml. each of the solution of formulation K and the solution containing formulations L and M are added to a clean, dry test tube. 10 microliters of serum are added to the tube and the resultant mixture is blended thoroughly and incubated at 37°C. for exactly 15 minutes. The optical density of the test system is then read at 445 nm against a reagent blank set at 100% transmission and the proportion of true glucose in the specimen determined from a standard curve.

Glucose standard curves are linear up to 300 mg% using the formulations and assay procedure of this example. Sera with high glucose levels (>300 Mg%) should be diluted with saline (0.9% NaCl) before analysis and the calculation corrected with the dilution factor.

EXAMPLE 7

Inorganic Phosphorus Formulations and Assay

Two separate formulations are provided for the inorganic phosphorus test. The two formulations which are utilized are set forth in Table 1 as formulations N and O. Predetermined amounts of these formulations are dissolved in separate portions of water to provide liquid reagents for use in making the inorganic phosphorus assay.

In the preparation of reducer quench formulation N, L-ascorbic acid (3.25 kg.), milled sulfamic acid (800 g.) and dry "Duponol ME" (775 g.) were blended in a Hobart bowl and thoroughly agitated to promote intimate mixing. With the mixer running, a solution of "Tetronic 707" (125g.) in methylene chloride (1000 ml.) was added. Additional methylene chloride (500 ml.) was subsequently introduced to produce the desired degree of granulation and wetness. The wet granulation was screened and dried and the resultant dry granulation rescreened and packaged in the manner described in Example 1 for hemoglobin reagent formulation A.

To prepare chromogenic reagent formulation O, the sodium molybdate constituent of the formulation was dried in the manner described in Example 5. Tris(hydroxymethyl)-aminomethane (1.50 kg.), "Duponol ME" (470 g.) and dried sodium molybdate (950 g.) were then blended in a Hobart bowl and thoroughly agitated to promote intimate mixing. With the mixer running, a solution of "Tetronic 707" (80.0 g.) in methylene chloride (475 m.) was added. Additional methylene chloride (175 ml.) was then introduced to produce the desired degree of granulation and wetness. The wet granulation as screened and dried and the resultant dry granulation rescreened and packaged in the manner described in Example 1 for hemoglobin reagent formulation A.

Dissolved in separate portions of water, reagent formulations N and O yield liquid reagents useful in assaying a body fluid for inorganic phosphorus. Sodium molybdate from the solution of chromogenic formulation N reacts with inorganic phosphorus from the specimen to produce phosphomolybdic acid. Phosphomolybdic acid is in turn reduced by the ascorbic acid component of the solution of reducer quench formulation 0 to produce a phosphomolybdenum blue, the color of which is indicative of the inorganic phosphorus content of the specimen.

The liquid reagent solution of formulation N is prepared by dissolving 1.5 g. of the formulation in 150 ml. of water. The solution of formulation O is prepared by dissolving 4.9 g. of that formulation in 50 ml. of water. The chromogenic liquid reagent solution of formulation N is stable for 1 week at room temperature. The liquid reagent solution of formulation O should be prepared fresh daily and protected from light. The resulting solutions are sufficient for conducting 50 tests.

In the conduct of the test, 3 ml. of the solution of formulation O and 1 ml. of the solution of formulation N are added to a clean, dry test tube and intermixed 0.05 ml. (50 lambda) of serum is added to the reagent mixture and thoroughly mixed therewith. The resultant reagent/specimen test system is incubated at 37°C. for 20 minutes, after which the optical density of the system is measured at 700 nm and compared with a reagent blank set at 100% transmission. The inorganic phosphorus content of the specimen is then determined from a standard curve.

The phosphorus standard curves are linear up to 15% mg%.

EXAMPLE 8

Lactate Dehydrogenase Reagent Formulations and Assay

For the lactate dehydrogenase-(lactate as substrate) (LDH-L), two separate formulations are provided. The two formulations which are utilized are set forth in Table 1 as formulations P and Q. Predetermined amounts of these formulations are dissolved together in a single portion of water to provide the liquid reagent for use in making the LDH-L assay.

To prepare coenzyme formulation P, nicotinamide adenine dinucleotide, modified as described below (equivalent to 225 mg. nicotinamide adenine dinucleotide) and mannitol (sufficient to provide 25.0 mg./test) were blended in a Hobart bowl and agitated to promote intimate mixing. With the mixer running, a solution of "Tetronic 707" (60.0 g.) in methylene chloride (500 ml.) was added to the blend. Additional methylene chloride (approximately 250 ml.) was subsequently introduced to produce the desired degree of granulation and wetness. The wet granulation was then screened and dried at room temperature, and the resultant dry granulation rescreened and packaged in the manner described in Example 1 for hemoglobin reagent formulation A.

To prepare modified nicotinamide adenine dinucleotide (NAD), NAD free acid (10 g.) was dissolved in distilled water (approximately 150 ml.) and the resulting solution was titrated slowly with 10% sodium hydroxide solution to pH 6.4 to 6.5 (approximately 6.5 ml. of sodium hydroxide solution was required). Lactose (20.5 g.) was then added together with a sufficient amount of water to make a total volume of approximately 400 ml. The solution was stirred until all solids were completely dissolved. The resulting solution was transferred into freeze drying vessels and shell frozen by rotating the vessels in a dry ice/alcohol bath at −60°C. or below. The frozen product was lyophilized for 20 to 24 hours at −60°C. to −70°C. and an absolute pressure of 5 m $\mu$ Hg. The resultant lyophilized powder was collected under an atmosphere having a relative humidity of less than 5% and stored in a dessicator at 4°C. Approximately 30.8 g. of dry modified NAD powder was obtained.

To prepare substrate formulation Q, lithium lactate (2.25 kg.), tris-(hydroxymethyl)-aminomethane (225 g.), sodium bicarbonate (450 g.) and "Renex 35" (175 g.) were blended in a Hobart bowl and agitated to promote intimate mixing. With the mixer running, a solution of "Tetronic 707" (75 g.) and polyethylene glycol-6000 (25 g.) in methylene chloride (500 ml.) was added to the blend. Additional methylene chloride (approximately 1175 ml.) was subsequently introduced to produce the desired degree of graulation and wetness. The wet granulation was then screened and dried at room temperature, and the resultant dry granulation rescreened and packaged in the manner described in Example 1 for hemoglobin reagent formulation A.

Dissolved together in a single portion of water, formulations P and Q provide a liquid reagent useful in assaying a biological specimen for lactate dehydrogenase-L. Catalyzed by LDH-L from the specimen, lactate from substrate formulation Q and NAD from coenzyme formulation P are converted to pyruvate and NADH. The extent of this reaction, which corresponds to the LDH enzymatic activity of the specimen, is measured by observing an increase in optical density at 340 nm.

To prepare a quantity of liquid reagent sufficient for 50 tests, formulation P (1.25 g.) and formulation Q (3.20 g.) are added to the distilled water (150 ml.) in a suitable container and the container shaken gently until the granules are completely dissolved. The liquid reagent solution thus prepared should be used within 8 hours.

In the conduct of the test, 3 ml. of the liquid reagent solution is dispensed into a clean absorption cell. Both the reagent in the cell and the serum sample are separately preincubated in a heating unit at 37°C. for 7–10 minutes. After preincubation, 0.050 ml. (50 lambda) of a serum sample is transferred to the cell and thoroughly mixed with the liquid reagent at 37°C. to produce a specimen/reagent test system. Exactly 1 minute after the serum specimen is initially mixed with the reagent, the cell is removed from the heating unit and the absorbance of the specimen/reagent test system is read with a spectrophotometer which had previously been set at zero absorbance with distilled water. Immediately after this measurement is taken, the cell is returned to the heating unit and held there until exactly 3 minutes after the serum was first mixed with the reagent, i.e., 2 minutes after the first reading. Then the cell is again removed from the heating unit and a final absorbance reading taken. The LDH units present in the specimen are determined by the following calculation:

$$\frac{(A_2 - A_1) \times 4900}{L} = \text{LDH units per ml. serum}$$

where $A_1$ equals the absorbance read at 1 minute, $A_2$ equals the absorbance read at 3 minutes and L equals the light path in centimeters.

If the absorbancy difference ($A_2 - A_1$) exceeds 0.14, a very high LDH activity in the serum is indicated. At this level of activity, the relationship between the absorbancy difference and the LDH units per ml. serum is not linear and the coefficient in the above-noted equation may be inaccurate, yielding inaccurate results. To provide greater accuracy in the measurement of high LDH activities, the above-described test is repeated with a 20 µl serum sample and the activity calculated in accordance with the following equation:

$$\frac{(A_2 - A_1) \times 12,180}{L} = \text{LDH units per ml. serum}$$

As those skilled in the art will appreciate, the accuracy of this LDH test is also highly dependent on the temperature control. Preferably, therefore, the spectrophotometer which is used includes a temperature control means for the cuvette compartment in which the sample cell is held during measurement, and the temperature of the sample is controlled at 37°C. Where the instrument is not so-equipped with temperature control, the absorption cell should not be removed from the heating unit for more than 10 seconds when reading the sample.

The LDH unit is defined as that amount of enzyme which catalyzes the conversion of 0.001 micromoles per minute NAD to NADH under the above-described test conditions. The Wacker (or Amador) procedure, also known to the art, employs the same primary reaction but is carried out at 25°C. instead of 37°C. By definition, one Wacker (or Amador) unit is equivalent to 1.15 LDH units. Thus, to convert LDH units to Wacker units, the LDH units are multiplied by 0.87.

EXAMPLE 9

Serum Glutamic Pyruvic Transaminase Formulations and Assay

For the serum glutamic pyruvic transaminase test, two separate formulations are provided. The two formulations which are utilized are set forth in Table 1 as formulations R and S.

Preparatory to blending the constituents of coenzyme reagent formulation R, the modified lactate dehydrogenase and reduced nicotinamide adenine dinucleotide components are prepared. The modified NADH component was prepared in accordance with the method described in Example 4. Modified lactate dehydrogenase was prepared as described below.

Gum arabic (15 g.), ammonium sulfate (10 g.), tris-(hydroxymethyl)-aminomethane (12 g.), and bovine serum albumin (0.1 g.) were dissolved in distilled water (450 ml.). The resulting solution was titrated to a pH of 7.4 with 12N sulfuric acid and then diluted to a total volume of 500 ml. This solution was clarified by centrifugation at 10,000 rpm and a temperature of 10°C. for 16 minutes, using a No. 872 angle rotor in an IEC B–20 refrigerated centrifuge. To 300 ml. of the clarified solution was added an LDH crystalline suspension in ammonium sulfate solution (10 ml. containing 100 mg. LDH). The resulting enzyme mixture was stirred for 5 minutes to insure good mixing and then divided and each portion placed in one of several freeze-drying vessels. Each portion was then frozen in thin layers by rotating the vessel containing it in a dry ice/alcohol bat at −60°C. or below. The frozen thin layers were lyophilized at − 60°C. to −70°C. at a total pressure of 5 m$\mu$ Hg for a period of 18–20 hours. The lyophilized powder obtained was collected under an atmosphere having a relative humidity of less than 5% and stored in a dessicator at 4°C. Approximately 26 g. of dry powder was obtained. This powder was assayed for the enzymatic activities of both glutamic pyruvic transaminase and LDH. The GPT specific activity was found to be less than 0.04% in relation to the LDH specific activity and the modified LDH lyophilized powder was therefore suitable for use in preparing formulation R.

In the preparation of enzyme reagent formulation R, modified NADH (having an equivalent NADH content of 0.4 mg.), modified LDH (having an LDH equivalent of 2 units), DL-alanine (1.20 kg.), dibasic sodium phosphate (585 g.), and milled monobasic sodium phosphate (750 g.) were blended in a Hobart bowl and agitated to promote intimate mixing. With the mixer running, a solution of "Tetronic 707" (50.4 g.) in methylene dichloride (200 ml.) was added to the blend. Additional methylene chloride (approximately 70 ml.) was subsequently introduced to produce the desired degree of granulation. The wet granulation was then screened and dried at room temperature and the resultant dry granulation rescreened and packaged in the manner described in Example 1 for hemoglobin reagent formulation A.

Substrate reagent formulation S has essentially the same composition and was prepared in essentially the same manner as was formulation G of Example 4.

Dissolved in separate portions of water, formulations R and S provide liquid reagents useful in assaying for serum glutamic pyruvic transaminase (SGPT). SGPT present in the specimen catalyzes the transamination of L-alanine and α-ketoglutaric acid producing a pyruvate and glutamate. Pyruvate and NADH, in the presence of LDH, are converted to lactate and NAD. The extent of reaction is indicative of the SGPT present and is measured by observing a change in optical density at 340 nm at 37°C.

To prepare a coenzyme liquid reagent solution, formulation R (6.55 g.) is dissolved in distilled water (125 ml.). A substrate liquid reagent is prepared by dissolving formulation S (1.00 g.) in distilled water (25 ml.). The resulting solutions are sufficient for 50 tests. The substrate liquid reagent is stable for 1 week when refrigerated. The coenzyme reagent formulation, on the other hand, should be prepared fresh daily.

In the conduct of the test, an aliquot of the solution of formulation R (2.5 ml.) is mixed with a serum specimen (100 μl) to form a reagent/specimen test system which is then preincubated at 37°C. for 7–10 minutes in a heating unit. After preincubation, an aliquot of the solution of reagent formulation S (0.5 ml.) is added to the test system and mixed in less than 10 seconds at room temperature. The container holding the system is returned to the heating unit where it is held at 37°C. Exactly 2 minutes after the solution of formulation S is added, the container is removed from the heating unit and the absorbance of the test system measured using a spectrophotometer which has previously been set at zero absorbance using distilled water as a blank. Immediately after the measurement is taken, the container is returned to the heating unit and held at 37°C. Exactly 5 minutes after the solution of formulation S is added (i.e., three minutes after the first reading), the container holding the test system is again removed from the heating unit and the absorbance again measured on the spectrophotometer. The SGPT content of the system is then determined in accordance with the following calculations:

$$\frac{A_1 - A_2 \times 1665}{L} = \text{SGPT units per ml. serum}$$

where $A_1$ equals absorbance read at 2 minutes, $A_2$ equals absorbance read at 5 minutes and L equals the light path of the absorption cell or the I.D. of the container in centimeters.

An SGPT unit is defined as that amount of enzyme which catalyzes the oxidation of 0.001 micromoles per minute of NADH to NAD at 37°C. under the above test conditions. The Karmen procedure known to the art carries out the above reactions at 25°C. instead of 37°C. By definition, one Karmen unit is equal to 1.09 SGPT units, and SGPT units may therefore be converted to Karmen units by multiplying the SGPT units by 0.917.

If the absorbancy difference ($A_1 - A_2$) observed in the above determination exceeds 0.225 a very high SGPT activity in the serum is indicated. At this level of activity, the relationship between the absorbancy difference and the LDH units per milliliter of serum is not linear and the coefficient in the above-noted equation may be inaccurate, yielding inaccurate results. To provide greater accuracy in the measurement of high SGPT activities, the above-described test is repeated with a 20 μl serum sample and the activity calculated in accordance with the following equation:

$$\frac{A_1 - A_2 \times 8100}{L} = \text{SGPT units per ml. serum}$$

It will be appreciated that the accuracy of the SGPT test is also highly dependent on close temperature control. Preferably, therefore, the cuvette compartment of the spectrophotometer used includes means for temperature control and the temperature of the specimen is controlled at 37°C. Where the instrument is not so-equipped with temperature control means, the absorption cell should not be removed from the heating unit for more than 10 seconds when making an optical density determination on the test system.

EXAMPLE 10

Colorimetric Formulations and Assay for Uric Acid

For the colorimetric uric acid test, three separate formulations are provided. These three formulations are set forth in Table 1 as formulations T, U and V. Predetermined amounts of these formulations are dissolved in separate portions of water to provide liquid reagents for use in making the uric acid assay.

Preparatory to blending the constituents of enzyme reagent formulation T, the modified uricase component thereof was produced. To produce the modified uricase, a borate buffer was initially prepared by dissolving boric acid (50 g.) in distilled water (3.5 l.) and titrating the resulting solution to a pH of 9 with 10% solution of sodium hydroxide. The titrated solution was then diluted to a total volume of 4 l. (0.2 M in borate) and chilled in a refrigerator prior to use. Uricase (about 40 mg.) was transferred to a 250 ml. beaker by streams of the borate buffer delivered from a wash bottle. The uricase used was uricase solution in 50% glycerol obtained from Boehringer Mannheim Corporation (Cat. No. 15074 EVAC) and having a specific activity of about 4.5 U/mg. at 25°C. and about 10.5 U/mg. at 37°C. After the uricase was transferred, additional borate buffer was added to bring the total volume of uricase solution in the beaker to approximately 100 ml. The diluted uricase solution was then dialyzed against approximately 2 l. of 0.2 M borate buffer for 4 hours, contaminated buffer being replaced with fresh buffer at the end of the first 2 hours of dialysis. While dialysis was in progress potassium chloride (6 g.), mannitol (4 g.) and gum acacia (4 g.) were dissolved in 0.2 M borate buffer (100 ml.). The resulting solution was clarified by centrifugation at 10,000 rpm and 10°C. for 16 minutes using a No. 872 angle rotor in an IEC B-20 refrigerated centrifuge. Bovine serum albumin (0.4 g.) and approximately 67,200 units of catalase were added to the clarified solution to produce a solution referred to hereinafter as the inert solution.

After dialysis of the uricase solution was complete, the dialyzed uricase solution was transferred to a 500 ml. beaker and combined with a 200 ml. portion of the inert solution. Distilled water (200 ml.) was then added and the resulting solution was thoroughly mixed. This solution was then transferred into two separate freeze-drying vessels and shell frozen in a dry ice/alcohol bath at a temperature of −60°C. or below. The frozen solution was lyophilized at −60°C. to −70°C. and an absolute pressure of 5 millimicrons mercury for 20–24 hours. The resultant lyophilized powder was collected under an atmosphere having a relative humidity of less than 5% and stored in a dessicator at 4°C. Approximately 19.5 g. of modified uricase was obtained.

To prepare uricase reagent T, modified uricase (equivalent to 0.05 units/test), glycine (113.25 g.) and anhydrous sodium carbonate (39.75g.) were blended in a Hobart bowl and thoroughly agitated to promote intimate mixing. With the mixer running, a solution of "Tetronic 707" (4.50 g.) in methylene chloride (25 ml.) was introduced. Additional methylene chloride (approximately 10 ml.) was subsequently added to produce the desired degree of granulation and wetness. The wet granulation was then screened and dried and the resulting dry granulation rescreened and packaged in the manner described in Example 1 for hemoglobin reagent formulation A.

In the preparation of copper reagent formulation U, tris-(hydroxymethyl)-aminomethane (112.50 g.), sodium bicarbonate (112.5 g.) and anhydrous cupric sulfate (1.95 g.) were blended in a Hobart bowl and agitated to promote intimate mixing. With the mixer running, a solution of "Tetronic 707" (7.05 g.) in methylene chloride (15 ml.) was added. Additional methylene chloride (approximately 5 ml.) was subsequently introduced to produce the desired degree of granulation and wetness. The wet granulation was then screened and dried and the resulting dry granulation rescreened and packaged in the manner described in Example 1 for hemoglobin reagent formulation A.

To prepare neocuproine reagent formulation V, neocuproine hydrochloride (5.25 g.), "Renex-35" (150 g.) and "Tetronic 707" (4.75 g.) were blended in a Hobart bowl and thoroughly agitated to promote intimate mixing. Methylene chloride (approximately 40 ml.) was then introduced to produce the desired degree of granulation and wetness. The wet granulation was then screened and dried and the resulting dry granulation rescreened and packaged in the manner described in Example 1 for hemoglobin reagent formulation A.

Dissolved in separate portions of water, formulations T, U and V provide liquid reagents useful in assaying a biological specimen for uric acid. Uric acid in the specimen reduces cupric ion of formulation U to cuprous ion which in turn reacts with neocuproine of formulation V in buffered solution to form a color complex. The resulting optical density of the test system is compared with the optical density of a blank prepared in the same manner as the test system but further including uricase from formulation T which destroys uric acid. The differences in absorbances between the test system and the blank is proportional to the serum uric acid content.

To prepare the liquid enzymatic reagent, formulation T (1.18 g.) is dissolved in distilled water (150 ml.). A uricase blank solution (formulation W) is prepared by dissolving (1.18 g.) in distilled water (150 ml.). The copper-bearing liquid reagent is prepared by dissolving formulation U (1.55 g.) in distilled water (25 ml.). A neocuproine-bearing liquid reagent is prepared by dissolving formulation V (1.06 g.) in distilled water (25 ml.). The liquid reagent solutions of formulations U and V are stable indefinitely at room temperature while the solution of formulation T should be prepared fresh daily. The resulting solutions are sufficient for conducting 50 tests.

In the conduct of the test, a 3 ml. portion of the solution of formulation T is added to one test tube and 3 ml. portion of formulation W is added to a second test tube. 0.1 ml. of serum is then added to both tubes to provide a specimen/reagent test system in the tube containing distilled water and a blank test system in the tube containing the solution of formulation T. The contents of both test tubes are then incubated for 15 minutes at 37°C., following which 1 ml. of a combined color reagent mixture, prepared by mixing equal volumes of the solutions of formulations U and V, is added to both the specimen/reagent test system and the the blank test system. Both of the test systems are allowed to stand at room temperature for 15 minutes after addition of the combined color reagent mixture and the light absorbance of each system is then measured at 455 nm on a spectrophotometer set at 100% transmission on a water blank. To provide the data required for the calculation of uric acid in the serum, another optical density measurement is taken on a standard reagent blank. The standard reagent blank is prepared by adding uric acid (100 mg.) and lithium carbonate (60 mg.) to distilled water (about 500 ml.) and warming the mixture to 60°C. to dissolve the additives. The resulting solution is cooled to room temperature and diluted to a total volume of 1000 ml. with additional quantities of distilled water. 3 ml. of this reagent blank is then added to a test tube and processed in the same fashion as the blank and the specimen/reagent test system including addition of serum, incubation, addition of the above-noted combined color reagent mixture and a 15-minute hold prior to measurement of optical density. The mg% uric acid in the serum specimen is then determined in accordance with the following calculation:

$$\frac{\text{Test O.D. (vs. water)} - \text{Blank O.D. (vs. water)}}{\text{Standard O.D. (vs. reagent blank)}} \times 10 \text{ mg.}$$

EXAMPLE 11

U.V. Formulations and Assay for Uric Acid

Two formulations are used in the uric acid (U.V.) test. One of these formulations is formulation T of Example 10 while the other is set forth in Table 1 as formulation W. Predetermined amounts of these formulations are dissolved in separate portions of water to provide liquid reagents for use in making the uric acid (U.V.) assay.

In preparing formulation W, a uricase placebo is used. This is prepared in the same manner as the modified uricase component of formulation T as described in Example 10 except that the uricase is omitted.

To prepared formulation W, uricase placebo (19.50 g.), glycine (113.25 g.) and anhydrous sodium carbonate (39.75 g.) were blended in a Hobart bowl and thoroughly agitated to promote intimate mixing. With the mixer running, a solution of "Tetronic 707" (4.50 g.) in methylene chloride (25 ml.) was introduced. Additional methylene chloride (approximately 10 ml.) was subsequently added to provide the desired degree of granulation and wetness. The wet granulation was screened and dried and the resultant dried granulation rescreened and packaged in the manner described in Example 1 for hemoglobin reagent formulation A.

A liquid reagent solution of formulation W is used in conjunction with a liquid reagent solution of formulation T in practicing the uric acid (U.V.) test. In the presence of the uricase of formulation T, uric acid from the specimen reacts with water and oxygen to form allantoin, carbon dioxide, and hydrogen peroxide. Light absorbance at 293 nm, the absorption peak of uric acid, is measured before and after treatment of the specimen with uricase from formulation T with the difference in absorbance being proportional to the uric acid present in the system. Allantoin, the product of the uricase catalyzed reaction of water, uric acid and oxygen, does not absorb at 293 nm, The liquid reagent solution of formulation T is prepared as described in Example 10 above. To prepare a blank liquid reagent, formulation W (1.18 g.) is dissolved in distilled water (150 ml.). As noted above, the solution of formulation T should be prepared fresh daily. The liquid reagent solution of formulation W is stable for 1 month when refrigerated. The resulting solution is sufficient for conducting 50 tests.

In conducting the test, a blank system is prepared by mixing the solution of formulation W (3.0 ml.) with a specimen of serum (100 μl) while a specimen/reagent test system is prepared by mixing the solution of formulation T (3.0 ml.) with a specimen of the same serum (100 μl). Both the blank system and the specimen/reagent test system are incubated at 37°C. for 15 minutes. The incubated mixtures are then transferred to cuvettes of a spectrophotometer having a 1 centimeter light path. The instrument is zeroed at 0.800 O.D. with the blank at 293 nm. The absorbance of the unknown is then read and the mg% uric acid in the specimen is determined in accordance with the following calculation:

$$(0.8 - \text{O.D. of unknown}) \times 41.36$$

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. In a method of conducting a clinical diagnostic test on a biological specimen wherein the specimen is mixed with a liquid reagent formulation to form a specimen/reagent system, the liquid reagent formulation containing a reagent capable of effecting a reaction which causes a measurable change in the specimen/reagent system, and a change in the system resulting from the reaction is measured, the improvement which comprises preparing the liquid reagent formulation by dissolving in water a granular, water-soluble, substantially anhydrous, storage-stable mixture containing the reagent and a nitrogen-containing polyoxyalkylene nonionic surfactant obtained by the sequential reaction of ethylenediamine with propylene oxide and ethylene oxide in the presence of a catalyst, the surfactant containing polyoxypropylene chains having an average molecular weight of between about 750 and about 6750 and polyoxyethylene chains constituting between about 10 and about 80 weight percent of the surfactant.

2. A method as set forth in claim 1 wherein the nitrogen-containing surfactant is solid and the polyoxypropylene chains thereof have an average molecular weight of less than about 4000.

3. A method as set forth in claim 2 wherein the polyoxypropylene chains of the surfactant have an average molecular weight of about 2750 and the weight percentage of the polyoxyethylene units thereof is about 70%.

4. In a method of assaying a biological specimen for hemoglobin utilizing a liquid reagent formulation containing potassium ferricyanide and potassium cyanide the improvement which comprises preparing the liquid reagent formulation by dissolving in water, a granular, water-soluble, substantially anhydrous, storage-stable reagent formulation containing potassium ferricyanide, potassium cyanide, sodium bicarbonate, mannitol and a nitrogen-containing polyoxyalkylene nonionic surfactant obtained by the sequential reaction of ethylenediamine with propylene oxide and ethylene oxide in the presence of a catalyst, the surfactant containing polyoxypropylene chains having an average molecular weight of between about 750 and about 6750 and polyoxyethylene chains constituting between about 10 and about 80 weight percent of the surfactant.

5. A method as set forth in claim 4 wherein the polyoxypropylene chains of the surfactant have an average molecular weight of about 2750 and the weight percentage of the polyoxyethylene units thereof is about 70%.

6. In a method of assaying a biological specimen for protein utilizing a liquid reagent formulation containing cupric tartrate the improvement which comprises preparing the liquid reagent formulation by dissolving in water a granular, water-soluble, substantially anhydrous, storage-stable reagent formulation contaning cupric tartrate, sodium tartrate, lithium hydroxide, a surfactant comprising polyoxyethylene ether alcohol and urea, and a nitrogen-containing polyoxyalkylene nonionic surfactant obtained by the sequential reaction of ethylene diamine with propylene oxide and ethylene oxide in the presence of a catalyst, the surfactant containing polyoxypropylene chains having an average molecular weight of between about 750 and about 6750 and polyoxyethylene chains constituting between about 10 and about 80 weight percent of the surfactant.

7. A method as set forth in claim 6 wherein the polyoxypropylene chains of the surfactant have an average molecular weight of about 2750 and the weight percentage of the polyoxyethylene units thereof is about 70%.

8. In a method of assaying a biological specimen for phosphorus utilizing a first liquid reagent formulation containing sodium molybdate and a second liquid reagent formulation containing ascorbic acid, the improvement which comprises preparing the first liquid reagent formulation by dissolving in water a granular, water-soluble, substantially anhydrous, storage-stable reagent formulation containing sodium molybdate, tris-(hydroxymethyl)-aminomethane, sodium lauryl sulfate and a nitrogen-containing polyoxyalkylene nonionic surfactant obtained by the sequential reaction of ethylenediamine with propylene oxide and ethylene oxide in the presence of a catalyst, the surfactant containing polyoxypropylene chains having an average molecular weight of between about 750 and about 6750 and polyoxyethylene chains constituting between about 10 and about 80 weight percent of the surfactant, and preparing the second liquid reagent formulation by dissolving in water a second granular, water-soluble, substantially anhydrous, storage-stable reagent formulation containing ascorbic acid, sulfamic acid, sodium lauryl sulfate, and the nitrogen-containing polyoxyalkylene nonionic surfactant.

9. A method as set forth in claim 8 wherein the polyoxypropylene chains of the surfactant have an average molecular weight of about 2750 and the weight percentage of the polyoxyethylene units thereof is about 70%.

* * * * *